United States Patent [19]

Baertschi et al.

[11] Patent Number: 4,987,121

[45] Date of Patent: Jan. 22, 1991

[54] ERYTHROPOIETIC FACTOR

[75] Inventors: Alex J. Baertschi; Eero Niskanen, both of Charlottesville, Va.

[73] Assignees: Center for Innovative Technology, Herndon; University of Virginia, Charlottesville, both of Va.

[21] Appl. No.: 199,438

[22] Filed: May 27, 1988

[51] Int. Cl.$^5$ .............................. A61K 37/02
[52] U.S. Cl. ........................ 514/8; 514/12; 514/13; 530/397
[58] Field of Search ............... 514/8, 12, 13; 530/397, 530/326, 325, 324

[56] References Cited

U.S. PATENT DOCUMENTS

| 3,033,753 | 5/1962 | White et al. | 514/8 |
| 4,377,513 | 3/1983 | Sugimoto et al. | 514/8 |
| 4,465,624 | 8/1984 | Chiba et al. | 514/8 |
| 4,607,023 | 8/1986 | Thibault et al. | 514/12 |
| 4,652,549 | 3/1987 | Blaine | 514/13 |
| 4,663,437 | 5/1987 | de Bold | 530/324 |
| 4,670,540 | 6/1987 | Sahakibara | 530/324 |
| 4,721,704 | 1/1988 | Chang et al. | 514/11 |
| 4,732,889 | 3/1988 | Cynshi et al. | 514/8 |
| 4,757,048 | 7/1988 | Lewicki et al. | 514/11 |
| 4,804,650 | 2/1989 | Lewicki et al. | 514/15 |
| 4,824,937 | 4/1989 | Deghenghi et al. | 530/326 |
| 4,861,755 | 8/1989 | Breipohl et al. | 514/11 |

OTHER PUBLICATIONS

Hill, N., et al., Chem. Abs. 108(21): 180890v, 1988.
Niskanen, E., et al., Biochem. Biophys. Res. Commun., 156(1):15-21, Oct. 1988.
See list of 23 documents on the information disclosure statement.

Primary Examiner—Howard E. Schain
Assistant Examiner—Susan M. Perkins
Attorney, Agent, or Firm—Whitham & Marhoefer

[57] ABSTRACT

A method for treating anemia comprises administering an atrial natriuretic factor (ANF) alone or in combination with erythropoietin (Epo). The ANF potentiates the activity of Epo and causes production of erythroid progenitors, BFU-E and CFU-E, and as a consequence red blood cell production at greater levels than if Epo alone is present in the blood stream.

6 Claims, 2 Drawing Sheets

ERYTHROPOIETIC FACTOR

BACKGROUND OF THE INVENTION

1. Field of the Invention

The present invention generally relates to a method of using a recently discovered class of polypeptides for boosting red blood cell (erythrocyte) production and, more particularly, to using an atrial natriuretic factor (ANF) at a low concentration to potentiate the activity of erythropoietin (Epo).

2. Description of the Prior Art

In the United States alone, several million people suffer from anemia secondary to renal failure, chronic inflammatory disease and malignancies. Many hypotheses have been proposed for explaining the mechanism behind the development of anemia, and they include the blockade of iron in the reticuloendothelial system due to abnormal iron metabolism, impaired iron release, spleen involvement, impaired Epo production, hemolysis, and disorders in hemopoietic stem cells. Treatment of chronic anemia with blood transfusions may become unacceptable because of the risk of viral infections, such as AIDS or hepatitis, and other side effects, such as transfusion reaction or iron accumulation.

Epo is a large glycoprotein hormone synthesized in the kidney which affects the terminal stages of erythroid differentiation by enhanced cell division and maturation (see. Iscove, Cell Tissue Kinet. 10: 323, (1977)). Epo stimulates the proliferation of the late erythroid progenitor known as colony forming unit-erythroid (CFU-E) which are detectable by in vitro cell culture but not by microscopy, and morphologically recognizable erythroid cells which are derived from CFU-E after cell division and maturation (see, Jelkinan, Rev. Physiol. Biochem. Pharmacol 104: 139, (1986)).

Humoral control of the early stages of erythropoiesis is not as well understood. In vitro stimulation of the early erythroid progenitor known as burst forming unit-erythroid (BFU-E) has been observed in the presence of three species of molecules. Interleukin-3 (IL-3), also called multipotential growth factor (Multi-CSF), which acts on many hemopoietic precursors, stimulates BFU-E formation in vitro (see, Sieff, J. Clin. Invest. 79: 1549, (1987)). Granulocyte-macrophage colony stimulating factor (GM-CSF), which is thought to act mainly on granulocyte and macrophage precursors, stimulates BFU-E in vitro if cultures are initiated in the presence of this factor and Epo is added three to five days later (see, Donahue et al., Blood 66: 1479, (1985)). Erythroid potentiating activity factor (EPA) stimulates the growth of both BFU-E and CFU-E in vitro from both human and murine marrow and stimulates colony formation by the K-562 human erythroleukemic leukemia line cells (see, Gasson et al., Prog. Clin. Biol. Res. 184: 95, (1985), Gasson et al., Nature 315: 768, (1985), and Fraser et al., Blood 71: 104, (1988)). In vivo enhancement of erythropoiesis has been observed after administration of EPA to experimental animals (see, Niskanen et al., Clin Res 35: 429A, (1987) and Niskanen et al., Blood, (in press), (1988)). IL-3, GM-CSF and EPA are all large proteins that are difficult to produce in large quantities and are not easily introduced into the bloodstream by noninvasive means.

The sequence of red blood cell production can be summarized generally in the following manner. BFU-E originate from multipotential progenitor cells and give rise to CFU-E. The CFU-E then give rise to nucleated erythroid cells. The nucleated erythroid cells give rise to reticulocytes, and the reticulocytes give rise to red blood cells.

U.S. Pat. No. 4,732,889 to Cynshi et al discloses using Epo to treat anemia found in patients suffering from rheumatoid arthritis. Studies performed on adjuvant-induced arthritis rats showed that rats which had been injected intraperitoneally with human urinary derived Epo or cell derived recombinant Epo had significantly improved erythrocyte counts as compared with a control group. Currently, the treatment of choice for patients suffering from anemia is replacement therapy with recombinant Epo (see, for example, Eschbach et al., New Eng. J. Med. 316: 73-78, (1987) and Erslev, New Eng. J. Med. 316: 101-103, (1987)). Some of the disadvantages of replacement therapy with recombinant Epo include the high cost of Epo, the necessity of applying Epo by injection, and the possibility of developing antibodies which destroy Epo. Development of the antibodies may occur because large proteins, like Epo, are likely to be immunogenic.

Hypoxia is a deficiency in the amount of oxygen reaching bodily tissues. Stimulation of red blood cell production following hypoxia has been attributed to enhanced synthesis of Epo and its subsequent release from the kidney into the bloodstream (see, Jelkinan, Rev. Physiol. Biochem. Pharmacol. 104: 139, (1986)). ANF is another hormone released in response to low oxygen pressure (see, Baertschi et al., Biochem. Biophys. Res. Comm. 140: 427, (1986), and Baertschi et al., Am. J. Physiol., (in press), (1988)). ANF peptides are active hormonal substances which are synthesized in cardiac atria. Peptides which have been obtained from heart muscle have also been referred to as cardionatrin (de Bold et al., Life Sci., 33 297, (1983)), atriopeptin (Currie et al., Science 223 67, (1984)), and auriculin (Atlas et al, Nature 309: 717, (1984)). ANF is a family of polypeptides, all of which have a common amino acid sequence, but differ in length by the presence or absence of 1–8 amino acids on the amino or carboxyl termini (N-terminal or C-terminal, respectively).

U.S. Pat. No. 4,663,437 to de Bold discloses that extracts of ANF peptides play a role in extracellular fluid volume regulation. Shortly after administration, the extract enhances urinary flow and increases urinary sodium, potassium, and chloride excretion. U.S. Pat. No. 4,607,023 to Thibault et al discloses synthesized ANF peptides having diuretic, natriuretic, vasorelaxant, hypotensive or anti-hypertensive properties. These synthesized ANF peptides are administered systemically, either by intravenous, subcutaneous, or intramuscular injection, or by sublingual or nasal administration. U.S. Pat. No. 4,652,549 to Blaine discloses that ANF peptides can act as cardiac anti-hypertrophic agents. In addition, ANF peptides allow intravascular fluid to exit across capillaries leading to acute hematocrit rise (see, Fluckiger et al., Am. J. Physiol. H251:H880, (1986)).

SUMMARY OF THE INVENTION

It is an object of this invention to provide a method of using ANF-like polypeptides for boosting red blood cell production by potentiating the activity of Epo.

It is another object of this invention to provide a method of using ANF-like polypeptides together with Epo to greatly increase the production of erythroid progenitors (BFU-E and CFU-E), and as a consequence red blood cell production, over the production which would be obtainable using Epo alone.

It is yet another object of this invention to provide a method of treating anemia by application of low doses of ANF-like polypeptides alone or in combination with Epo.

According to the invention, ANF-like polypeptides have been found to affect the production of both early and late erythroid progenitors. In the absence of Epo, ANF has no effect on erythroid colony formation. In the presence of Epo, ANF increases BFU-E and CFU-E production up to four fold. The synergistic effect on Epo activity is dependent on the molecular form of ANF and on the concentration of ANF. Anemic patients may be treated by a combined application of low doses of Epo and ANF. In anemic patients with functional kidneys and detectable Epo, red blood cell production may be boosted by application of the ANF analog alone. It is anticipated that the patients which are treated with Epo and ANF or an ANF analog alone can be either human or animal subjects. The advantages over the prior replacement therapy with recombinant Epo are that Epo will be required at lower doses and at longer intervals, thereby reducing cost and minimizing immune reactions, and ANF analogs are easy to produce and can be administered non-invasively.

BRIEF DESCRIPTION OF THE DRAWINGS

The foregoing and other objects, aspects and advantages of the invention will be better understood from the following detailed description of the preferred embodiments of the invention with reference to the accompanying drawings, in which.

DETAILED DESCRIPTION OF THE PREFERRED EMBODIMENT OF THE INVENTION

The inventors have studied the effect of ANF-like polypeptides on human early and late erythroid progenitors, BFU-E and CFU-E, respectively, in vitro. In contrast to EPA, ANF release is controlled by a physiological mechanism, namely hypoxia, which plays a pivotal role in the regulation of erythropoiesis (see, Baertschi et al, Biochem. Biophys. Res. Comm. 140: 427, (1986) and Baertschi et al., Am. J. Physiol (in press), (1988)). Plasma ANF may increase up to 0.2 nanomolar (nM) due to hypoxia condition, and it is this response that led the inventors to assess whether ANF can control red blood cell mass by action on erythropoiesis.

Utilization of cell culture techniques allowed for the detection of molecules other than Epo which act on erythropoietic precursor cells. Demonstration of the stimulatory effect requires the presence of Epo in the system (see, Sieff, J. Clin. Invest. 79: 1549, (1987), Donahue et al, Blood 66: 1479, (1985), and Gasson et al, Prog. Clin. Biol. Res. 184: 95, (1985)). The erythroid progenitor BFU-E and CFU-E assay was utilized for the in vitro studies by the following method:

(1) Collect bone marrow cells from normal human volunteers after obtaining informed consent.

(2) Suspend cells in α-medium containing 10% fetal calf serum.

(3) Separate by Ficoll-Hypaque gradient to obtain an enriched mononuclear cell population.

(4) Culture cells ($5 \times 10^4$ per plate) in petri dishes using a methylcellulose technique (see, Iscove, J. Cell Physiol 83: 309, (1974)).

(5) Add Human Epo, available from the Toyoba Corp. of New York, N.Y., to the culture on day zero.

(6) Add ANF-like peptides on days zero, two, five, eight, and eleven.

Figure 1:
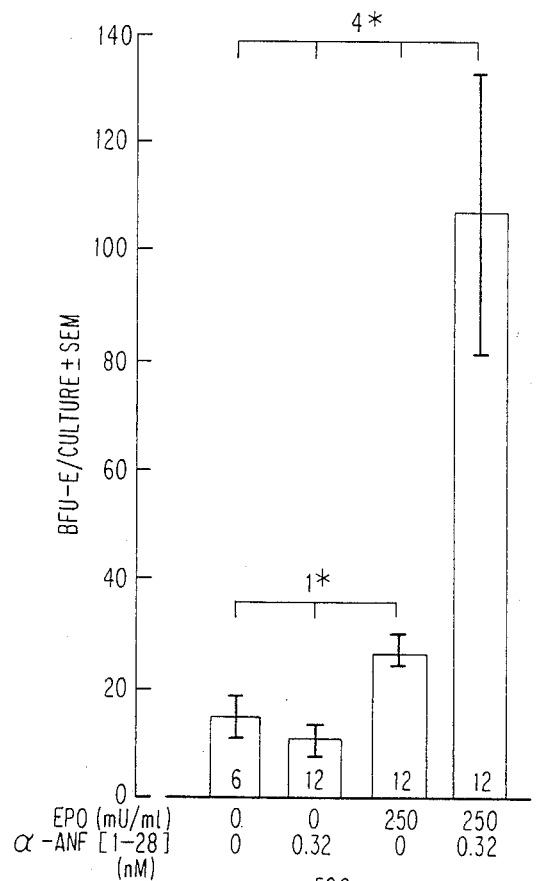
FIG. 1 is a bar graph showing the effect of ANF on the production of the BFU-E erythroid progenitors.
Figure 2:
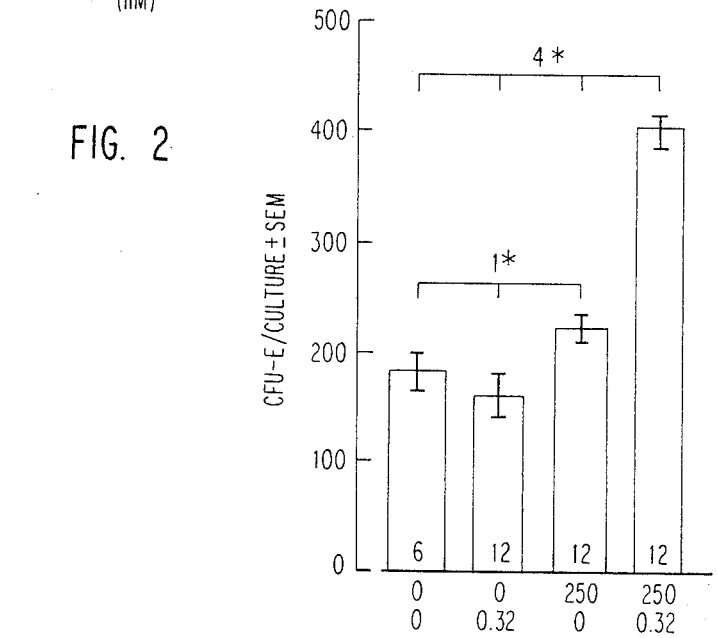
FIG. 2 is a bar graph showing the effect of ANF on the production of the CFU-E erythroid progenitor.

FIGS. 1 and 2 show that ANF in the presence of Epo caused a dramatic increase in BFU-E and CFU-E numbers relative to the productivity of Epo alone. In the absence of Epo, ANF has no effect on erythroid colony formation. In FIG. 1, the effects of α-ANF[1-28] alone and in conjunction with an added amount of Epo were studied. Human α-ANF[1-28] diluted in α-medium, obtained from the Peninsula Corporation, was added to the cultures every three days starting at day zero. Control cultures were supplemented with Phosphate Buffered Saline (PBS) alone. PBS is available from the GIBCO corporation of Grand Island, N.Y. Triplicate plates were incubated at 37° C. in a humidified atmosphere of 7% $CO_2$ in air. On the eighth day, cell aggregates which contained more than seven erythroid cells were counted as CFU-E. On the fourteenth day, aggregates of forty cells or more were counted as BFU-E. Hemoglobinization of the cells was confirmed by using a Soret band and morphologically from stained smears. In FIG. 1, the number of observations is indicated in the bottom part of the bar. The standard estimates from mean (SEM) are indicated as error bars. Statistical significances were obtained by using Kruskal-Wallis Analysis of Variance (one way by ranks). Probabilities in FIGS. 1 and 2 are indicated by: $1^* = p < 0.05$; $2^* = p < 0.01$; $3^* = p < 0.005$; and $4^* = p < 0.001$. As shown in FIG. 1, addition of human α-ANF[1-28] alone at a concentration of 0.32 nM to the cultures had no effect on erythroid precursors. Epo alone, at a concentration of 250 biological units (mU/ml), stimulated both erythroid precursors. The highest numbers for both BFU-E and CFU-E were observed in cultures containing Epo plus α-ANF[1-28]. The four-fold increase in BFU-E and the two-fold increase in CFU-E indicated that ANF may modulate erythropoiesis by potentiating Epo activity in the production of erythroid progenitors. The relative increase of Epo activity caused by the presence of ANF is the subject of this invention.

Figure 3:
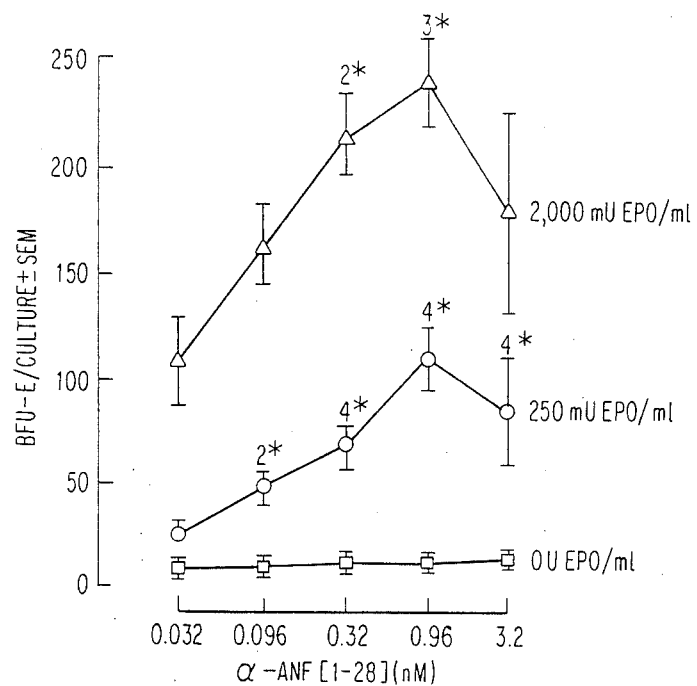
FIG. 3 is a line graph showing the effect of different concentrations of ANF on the production of the BFU-E erythroid progenitor when present in combination with different concentrations of EPO.
Figure 4:
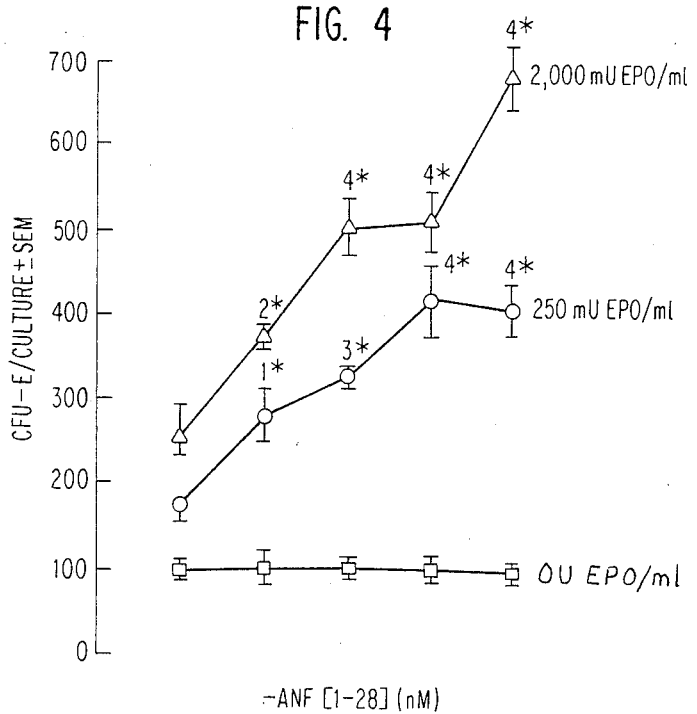
FIG. 4 is a line graph showing the effect of different concentrations of ANF on the production of the CFU-E erythroid progenitor when present in combination with different concentrations of EPO.

FIGS. 3 and 4 show that the stimulatory effect is dependent on the dose of α-ANF[1-28] and Epo. The BFU-E and CFU-E assay was prepared identically to the assay used for the determination shown in FIG. 1. The numbers were determined using the lowest ANF concentration as a reference point in each group. There were six observations per group. As shown in FIG. 2, for identical α-ANF[1-28] concentrations, BFU-E and CFU-E yield was higher in cultures containing 2,000 mU/ml of Epo than in cultures containing 250 mU/ml of Epo. When α-ANF[1-28] levels were increased from 0.032 nM to 0.96 nM, a concentration dependent potentiation of erythropoiesis was observed. For α-ANF[1-28] concentrations above 0.96 nM, potentiation leveled off or even declined. The number values for BFU-E and CFU-E in a culture containing 0.25 U/ml Epo and 0.32 nM α-ANF[1-28] are different for FIGS. 1 and 2 because different human volunteer bone marrow donors were used for each study. The absolute numbers are not the focus of this invention, rather, the subject of this invention is the relative increase in the production of BFU-E and CFU-E caused by Epo in the presence of ANF.

Table 1 shows that stimulation of erythroid colony formation by α-ANF[1-28] was not dependent on the presence of T lymphocytes or macrophages.

TABLE 1

THE EFFECT OF HUMAN α-ANF[1-28] AND ERYTHROPOIETIN ON PERIPHERAL BLOOD BFU-E IN THE ABSENCE OF T CELLS AND MACROPHAGES

| Agent | BFU-E/culture ± SEM |
|---|---|
| Experiment 1 | |
| Epo 250 mU/ml | 7.0 ± 0.9 |
| Epo 250 mU/ml + ANF 0.32nM | 22.7 ± 1.9** |
| Experiment 2 | |
| Epo 250 mU/ml | 14.0 ± 2.0 |
| Epo 250 mU/ml + ANF 0.32nM | 42.3 ± 6.8* |

T lymphocytes and macrophages have been shown to elaborate factors stimulating both BFU-E and CFU-E in vitro. The BFU-E assay was prepared similarly to the assay used for the determination shown in FIG. 1. The cultures contained peripheral blood derived cells instead of bone marrow cells. After Ficoll-Hypaque separation, preparations from peripheral blood were further incubated in plastic dishes twice for thirty minutes to remove macrophages. The majority of T cells were removed by rosetting with sheep red blood cells, available from the Lampire Corporation of Pipersville, Pa., and centrifugation. The remaining T-cells were removed by incubating the cell suspension with Leu-1 antibody, available from Becton-Dickenson, Inc. of Mountain View, Calif., and rabbit complement. Less than 0.3% of macrophages and T cells could be detected in the remaining cell suspension. The probabilities in Table 1 are as follows: $*=p<0.025$ and $**=p<0.005$. There were three observations per group. As shown by Table 1, the number of peripheral blood derived BFU-E increased three fold in the presence 0.32 nM of α-ANF[1-28] in cultures containing 250 mU/ml of Epo and less than 0.3% of T cells and macrophages.

Table 2 shows that potentiation of erythropoiesis depends on the specific molecular form of ANF which is present with Epo.

TABLE 2

POTENTIATION OF ERYTHROPOIETIN-STIMULATED ERYTHROPOIESIS FROM HUMAN BONE MARROW BY ANF-ANALOGS

| ANF Analog | Potentiation of BFU-E(%) | $p^1$ | $p^2$ |
|---|---|---|---|
| ANF[1-28] | 100 ± 24.9 | 0.001 | — |
| ANF[4-28] | 74.8 ± 15.3 | 0.003 | NS |
| ANF[5-28] | 98.5 ± 38.6 | 0.003 | NS |
| ANF[1-11] | −1.5 ± 8.8 | NS | 0.001 |
| ANF Dimer | 40.2 ± 26.7 | NS | 0.04 |

| ANF Analog | Potentiation of CFU-E(%) | $p^1$ | $p^2$ |
|---|---|---|---|
| ANF[1-28] | 100 ± 39.2 | 0.00003 | — |
| ANF[4-28] | 208 ± 41.0 | 0.00001 | 0.05 |
| ANF[5-28] | 143 ± 26.7 | 0.00001 | NS |
| ANF[1-11] | 14.8 ± 4.6 | NS | 0.003 |
| ANF Dimer | 25.4 ± 13.1 | NS | 0.025 |

Table 2 summarizes the effects of various ANF analogs, all of which are available from the Peninsula Corporation, on Epo stimulated erythroid colony formation from bone marrow. The BFU-E and CFU-E assay was prepared identically to the assay used for the determination shown in FIG. 1. The concentration of the ANF analog added to the cultures was 0.32 nM. All cultures were supplemented with 250 mU/ml of Epo. Potentiation is shown relative to the effect of α-ANF[1-28] alone (100%), where the actual numbers of BFU-E and CFU-E in the presence of α-ANF[1-28] and Epo were 103±26 and 440±176, respectively. The probabilities are indicated as $p^1$ and $p^2$, where $p^1$ is the statistical significance relative to Epo alone and $p^2$ is the significance relative to potentiation by α-ANF[1-28]. There were six observations per group. As shown in Table 2, the stimulatory effect of Epo on both BFU-E and CFU-E was enhanced by α-ANF[1-28], α-ANF[4-28], and α-ANF[5-28]. The effect of α-ANF [1-11] and α-ANF dimer on erythroid precursors was not significant.

The results indicate that all major circulatory forms of ANF, of which α-ANF[1-28], α-ANF[4-28], and α-ANF[5-28] are examples, stimulate erythroid colony formation in the presence of Epo. The bioactivity of ANF does not depend on an intact N-terminal sequence, but may require an intact ring structure, as does the bioactivity of ANF in the kidney. The removal of macrophages and T cells did not abolish the enhanced colony formation. This shows that the stimulating effect of ANF is not mediated via these cells. Preliminary experiments with ANF peptides having intact C-terminal sequences have shown similar effects. It is anticipated that any peptide which has significant homology with any part of the α-ANF[1-28] amino acid sequence will have the Epo enhancing characteristics which have been discovered and demonstrated. This includes all pharmaceutically acceptable salts, esters or amides thereof.

Anemia may be treated by administering small doses of Epo together with ANF to the patient. The ANF will potentiate the activity of the Epo, causing larger quantities of erythroid progenitors to be formed than if Epo was administered alone. The ANF analogs may be administered by injection, nasal inspiration, suppository methods, transdermally and possibly orally. The advantage of this method of treatment over treating patients with Epo alone is that far less Epo is required, thus saving substantial expense and multiple Epo injections Anemia may be treated by injecting a patient with Epo and, then having the patient inspire ANF into the blood stream through the nasal passage. Because the production of erythroid progenitors, BFU-E and CFU-E, is up to four times as great with Epo acting in the presence of ANF, Epo injections will be required far less frequently. In anemic patients with functional kidneys and detectable Epo, red blood cell production may be boosted by application of the ANF analog alone. While the human body produces ANF naturally, it only produces large amounts as a physiological response to hypoxia or blood volume expansion. Therefore, the body may not supply sufficient amounts of ANF in anemic patients with functional kidneys and detectable Epo. Administration of ANF-like polypeptides to these patients should be effective for boosting red blood cell production. Administering ANF to a patient by injection, nasal inspiration, sublingual application by suppository or by oral route is an effective way for the patient to have large amounts of ANF in his or her blood stream to potentiate the activity of the available Epo.

While the invention has been described in terms of specific ANF analogs boosting the activity of Epo, those skilled in the art will recognize that other ANF analogs may be used within the spirit and scope of the invention.

Having thus described our invention, what we claim as novel and desire to secure by Letters Patent is the following:

1. A method for enhancing red blood cell production in a tissue, comprising the steps of adding a quantity of an atrial natriuretic factor polypeptide and adding a quantity of erythropoietin to a tissue, said atrial natriuretic factor polypeptide being selected from the group consisting of α-ANF[1-28], α-ANF[4-28], and α-ANF[5-28].

2. A method as recited in claim 1 wherein the addition of said second quantity of erythropoietin achieves a concentration of greater than 250 mU/ml in said tissue.

3. A method as recited in claim 1 wherein said quantity of said atrial natriuretic factor added to said tissue achieves a concentration between 0.032 nanomolar and 3.2 nanomolar in said tissue.

4. A method as recited in claim 3 wherein said quantity of said atrial natriuretic factor added to said tissue achieves a concentration of approximately one nanomolar in said tissue.

5. A method as recited in claim 1 wherein said tissue is comprised of bone marrow.

6. A method as recited in claim 1 wherein said steps of adding said atrial natriuretic factor polypeptide and adding said erythropoietin to said tissue occur simultaneously.

* * * * *